US00PP11754P2

(12) United States Plant Patent
Rother

(10) Patent No.: US PP11,754 P2
(45) Date of Patent: Jan. 30, 2001

(54) ARGYRANTHEMUM PLANT NAMED 'HARVEST SNOW'

(76) Inventor: Reinhard W. Rother, 56 Emerald Monbulk Road, Emerald, Victoria 3782 (AU)

( * ) Notice: Under 35 U.S.C. 154(b), the term of this patent shall be extended for 0 days.

(21) Appl. No.: 09/334,025

(22) Filed: Jun. 15, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 10,298 * 3/1998 Cunneen ..... Plt./263
P.P. 10,720 * 12/1998 Hammond ..... Plt./263
P.P. 10,905 * 5/1999 Hammond ..... Plt./263
P.P. 11,085 * 10/1999 Cunneen ..... Plt./263

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Marguerite Daisy plant named 'Harvest Snow', characterized by its upright to outwardly spreading, very uniform, mounding and rounded, and very compact plant habit; freely branching growth habit; thick and somewhat succulent foliage and lateral branches; uniform daisy-type inflorescences with white ray florets and bright yellow disc florets; freely flowering with numerous inflorescences per plant held above the foliage on strong and erect peduncles; continuous and uniform flowering over a long period of time; long-lasting inflorescences; and heat-tolerance.

1 Drawing Sheet

BACKGROUND OF THE INVENTION

The present invention relates to a new and distinct cultivar of Argyranthemum plant, commonly referred to as a Marguerite Daisy, botanically known as *Argyranthemum frutescens*, and hereinafter referred to by the cultivar name 'Harvest Snow'.

The new cultivar is a product of a planned breeding program conducted by the Inventor in Emerald, Victoria, Australia. The objective of the breeding program was to develop compact, freely and continuously flowering Marguerite daisies that are heat-tolerant.

The new cultivar originated from a cross made by the Inventor in 1993 of an unnamed selection of *Argyranthemum frutescens*, as the male or pollen parent, with the *Argyranthemum frutescens* cultivar 'Frosty II', not patented, as the female or seed parent. The cultivar 'Harvest Snow' was discovered and selected by the Inventor as a flowering plant within the progeny of the stated cross in a controlled environment in Emerald, Victoria, Australia, in 1993.

Plants of the new Marguerite Daisy can be compared to plants of the female parent, the cultivar 'Frosty II'. In side-by-side comparisons conducted in Emerald, Victoria, Australia, plants of the new Marguerite Daisy have a more uniform plant habit, thicker leaves and larger inflorescences than plants of the cultivar 'Frosty II'.

Plants of the new Marguerite Daisy can also be compared to plants of the male parent, the unnamed selection of *Argyranthemum frutescens*. In side-by-side comparisons conducted in Emerald, Victoria, Australia, plants of the new Marguerite Daisy are more compact and have a more uniform plant habit than plants of the unnamed selection of *Argyranthemum frutescens*.

Asexual reproduction of the new cultivar by terminal cuttings in Emerald, Victoria, Australia, has shown that the unique features of this new Marguerite Daisy are stable and are reproduced true to type in successive propagations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Harvest Snow' which distinguish 'Harvest Snow' as a new and distinct cultivar:

1. Upright to outwardly spreading; very uniform; mounding and rounded; and very compact plant habit.
2. Freely branching, dense plants.
3. Thick and somewhat succulent foliage and lateral branches.
4. Uniform daisy-type inflorescences with white ray florets and bright yellow disc florets.
5. Freely flowering with numerous inflorescences per plant held above the foliage on strong and erect peduncles.
6. Continuous and uniform flowering over a long period of time.
7. Long-lasting inflorescences; inflorescences typically last about two to three weeks on the plant.
8. Very heat-tolerant.

BRIEF DESCRIPTION OF THE PHOTOGRAPHS

The accompnaying colored photographs illustrate the overall appearance of the new cultivar, showing the colors as true as it is reasonably possible to obtain in colored reproductions of this type.

The photograph at the top of the sheet comprises a side perspective view of three typical plants of 'Harvest Snow' in a 20-cm container.

The photograph at the bottom of the sheet comprises close-up views of developing inflorescences (top) and developing leaves (bottom). Floret and foliage colors in the photographs may appear different from the actual colors due to light reflectance.

DETAILED BOTANICAL DESCRIPTION

The following observations, measurements and values describe three plants of the new Marguerite Daisy grown in a 20-cm container in Bonsall, Calif., in full sun with day temperatures ranging from 21 to 35° C. and night temperatures ranging from 13 to 18° C. Observations were made on plants 8 to 12 weeks after planting. Color references are made to The Royal Horticultural Society Colour Chart except where general terms of ordinary dictionary significance are used.

Botanical classification: *Argyranthemum frutescens* cultivar 'Harvest Snow'.

Parentage:

*Male or pollen parent.*—Unnamed selection of *Argyranthemum frutescens.*

*Female or seed parent.*—*Argyranthemum frutescens* cultivar 'Frosty II', not patented.

Propagation:

*Type.*—Terminal cuttings.

*Time to initiate/develop roots.*—Summer: About 15 days at a temperatures of 25° C. Winter: About 15 to 20 days at a temperatures of 20 to 25° C.

*Root description.*—Numerous, fine and freely branching.

Plant description:

*General appearance.*—Upright to outwardly spreading, very uniform, mounding, rounded and very compact plant habit. Freely branching, dense and full plant habit. Pinnatifid foliage. Erect and strong flower stems hold inflorescences above the foliage. Appropriate for various sizes and types of containers.

*Crop time.*—About 8 weeks are required to produce a finished flowering plant in a 10-cm container from a rooted cutting.

*Plant height.*—About 28 cm from soil level to top of inflorescences.

*Plant width.*—About 30 cm.

*Branching.*—Very freely basal branching; removal of the terminal apex (pinching) enhances branching. About 14 to 16 lateral branches typically develop after pinching.

*Vigor.*—Good vigor.

*Lateral branches.*—Length: About 24 cm. Diameter: About 5 mm. Internode length: About 2 cm. Texture: Glabrous; somewhat succulent; woody at base.

*Color.*—Green, 145B, no anthocyanin.

*Foliage description.*—Arrangement: Alternate, single. Quantity of leaves per lateral branch: Numerous, about 45. Shape: Pinnatifid. Apex: Broadly acute; two-parted. Base: Attenuate; clasping; sessile. Margin: Deeply incised. Length: About 5.8 cm. Width: About 3.2 cm. Thickness: Thick, about 1.5 mm, somewhat succulent. Texture: Glabrous, smooth. Durability to stresses: Good, very durable; thick cuticle. Color: Young leaves, upper surface: 137A. Young leaves, lower surface: 137B. Mature leaves, upper surface: 137B. Mature leaves, lower surface: 137C. Venation, upper surface: 137B. Venation, lower surface: 137C.

Flowering description:

*Flowering habit.*—Inflorescences on long peduncles held above the foliage. Flat, single-type composite inflorescence form. Inflorescences form at upper leaf axils. Florets arranged acropetally on a capitulum. Inflorescences very long-lived; inflorescences last about 2 to 3 weeks on the plant. Inflorescences persistent.

*Quantity of inflorescences.*—Very freely flowering; typically about 9 inflorescences and buds per lateral stem; usually about 135 inflorescences and buds per plant.

*Natural flowering season.*—Natural flowering season is spring to early fall. Plants flower continuously during this period.

*Inflorescence size.*—Diameter: About 3.5 cm. Depth (height): About 1.2 cm. Disc diameter: About 1.4 cm.

*Fragrance.*—None.

*Ray florets.*—Aspect: Flat. Quantity per inflorescence and arrangement: About 22 ray florets arranged in a single whorl. An additional whorl of small upright ray florets, about 1 cm in length and about 1 mm in width, are present interior to whorl of ray florets. Shape: Ligulate to elliptic. Apex: One-dentate. Base: Acute. Margin: Entire. Aspect: Flat or slightly upward. Length, outer florets: About 1.5 cm. Width, outer florets: About 5 mm. Texture: Smooth, satiny. Color: When opening, upper surface: 155D. When opening, lower surface: More white than 155D. Fully opened, upper surface: 155D. Fully opened, lower surface: More white than 155D.

*Disc florets.*—Shape: Tubular, 5-lobed. Quantity per inflorescence: Numerous, usually about 250. Disc floret length: About 6 mm. Disc floret width: About 1 mm. Color: Immature: 14A. Mature: 14B.

*Phyllaries.*—Quantity per inflorescence: About 18 per inflorescence. Arrangement: Imbricate, three rows; tightly pressed to the receptacle. Shape: Elliptic. Apex: Broadly acute. Margin: Entire, outer edges slightly membranous. Aspect: Cupped. Length: About 7 mm. Texture: Smooth. Color: Upper surface: 139B. Lower surface: 139C.

*Peduncle.*—Length, first peduncle: About 7.5 cm. Length, second peduncle: About 10 cm. Length, third peduncle: About 9 cm. Strength: Moderate to strong; inflorescences held well above foliage. Angle: Acute. Texture: Smooth. Color: 144A.

*Inflorescence bud.*—Shape: Nearly round. Length: About 9 mm. Diameter: About 9 mm. Color: 155A.

*Reproductive structures.*—Androecium: Present on disc florets. Stamens: About five; minute. Anther shape: Elongate. Anther size: About 1 mm. Anther color: 13B. Pollen: Scarce. Pollen color: 13B. Gynoecium: Present on ray and disc florets. Pistil number: One per floret. Pistil length: About 4 mm. Style length: About 3 mm. Style color: 12B. Stigma shape: Bi-parted. Stigma color: 12A. Ovary color: 145C.

Disease resistance: Resistance to pathogens common to Argyranthemum has not been observed.

Seed production: Seed production has not been observed.

Heat tolerance: Plants of the new Marguerite Daisy have been shown to be very heat-tolerant.

It is claimed:

1. A new and distinct Marguerite Daisy plant named 'Harvest Snow', as illustrated and described.

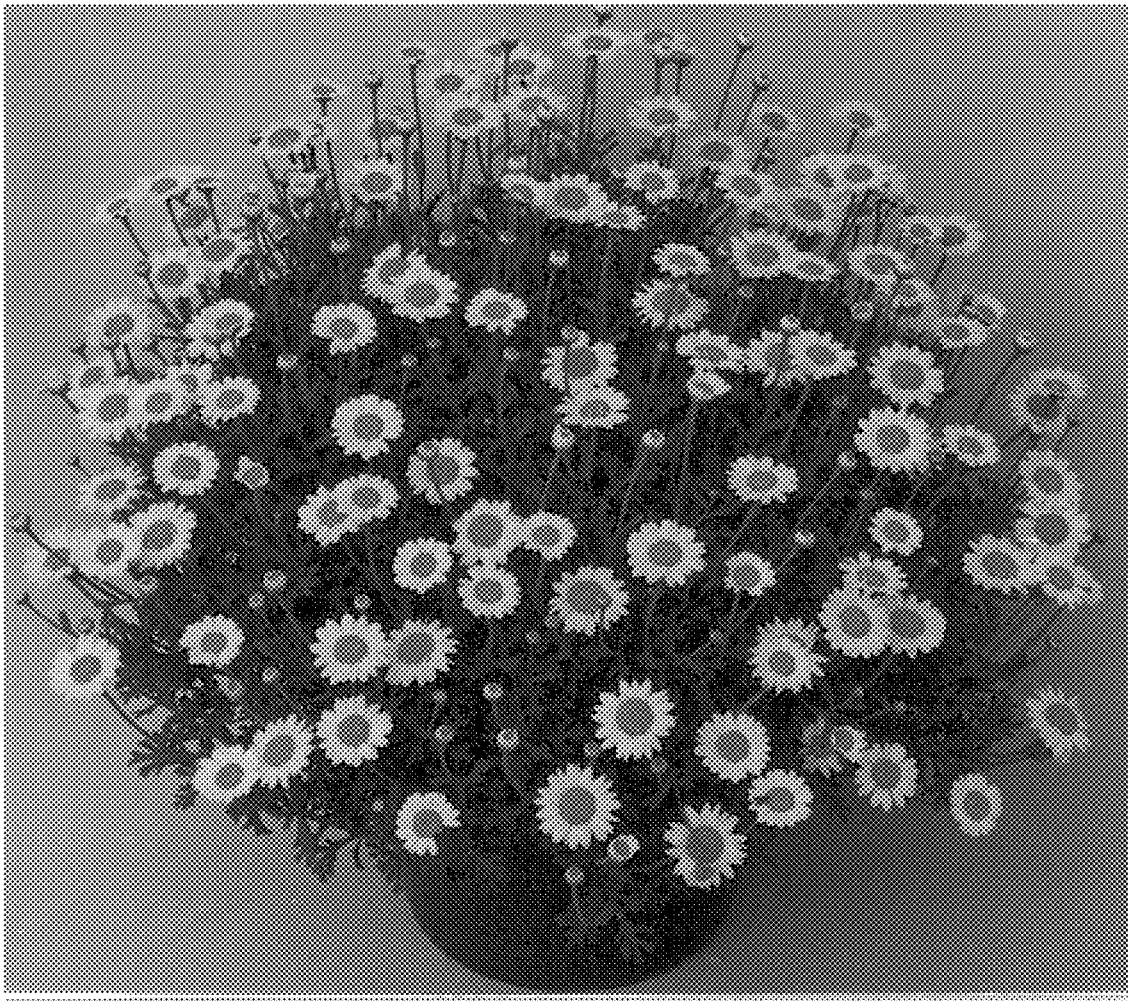
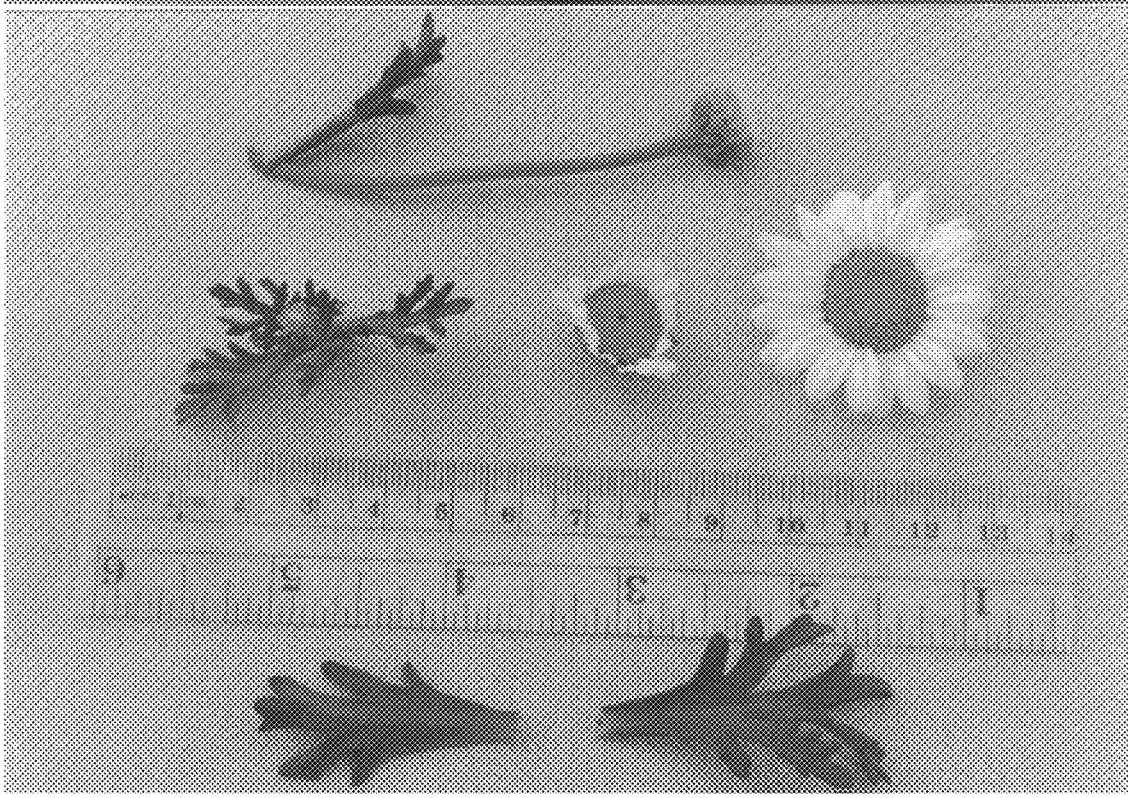

* * * * *